United States Patent
Lundbäck

[11] Patent Number: 5,891,028
[45] Date of Patent: Apr. 6, 1999

[54] INTERFACE ELEMENT FOR A BIOMEDICAL ELECTRODE

[75] Inventor: Stig Lundbäck, Vaxholm, Sweden

[73] Assignee: Humanteknik AB, Stockholm, Sweden

[21] Appl. No.: 765,510
[22] PCT Filed: Jul. 3, 1995
[86] PCT No.: PCT/SE95/00821
  § 371 Date: Dec. 27, 1996
  § 102(e) Date: Dec. 27, 1996
[87] PCT Pub. No.: WO96/01077
  PCT Pub. Date: Jan. 18, 1996

[30] Foreign Application Priority Data

Jul. 1, 1994 [SE] Sweden .................................. 9402339

[51] Int. Cl.$^6$ .................................................. A61B 5/0416
[52] U.S. Cl. ............................................................ 600/387
[58] Field of Search ..................... 600/372, 373, 600/384, 386, 387, 397; 601/149, 153

[56] References Cited

U.S. PATENT DOCUMENTS

| 2,887,112 | 5/1959 | Smith | 600/384 |
| 3,340,868 | 9/1967 | Darling . | |
| 3,998,215 | 12/1976 | Anderson et al. | 600/397 |
| 4,899,753 | 2/1990 | Inoue et al. | 600/387 |
| 5,289,822 | 3/1994 | Highe et al. | 607/153 |

FOREIGN PATENT DOCUMENTS

| 3920755 | 5/1990 | Germany | 607/149 |
| 2240928 | 8/1991 | United Kingdom . | |

Primary Examiner—Lee Cohen
Attorney, Agent, or Firm—Hill & Simpson

[57] ABSTRACT

Biomedical measurements such as ECG or EEG measurements are frequently performed using a suction electrode. An electrolyte is applied to the skin of the patient and a suction electrode is placed thereon to form an electrically conducting connection between the skin and the electrode. In accordance with the present invention and hygienic improvement is provided by introducing an interface element between the skin of the patient and the reusable electrode. The interface element is preferably provided in the form of a lamellar substrate for an electrolyte having a skin contact surface and an opposed electrode contact surface. The substrate further includes a central portion, a peripheral margin portion and an intermediate portion disposed between the central portion and the peripheral margin portion. The peripheral margin portion is adapted to form a vacuum seal against the skin of the patient with a seal portion of an applied biomedical electrode. The intermediate portion is permeable to air and expandable to a dome shape so that on forming a vacuum seal with a biomedical electrode any air disposed between a patients skin and the skin contact surface of a substrate may be evacuated. Upon evacuation of the suction electrode the patients skin and the substrate are drawn inwardly into the electrode until the electrode contact surface along the central portion of the substrate electrically contacts the electrode member of the suction electrode. The interface element contains sufficient electrolyte and ensures that an ample amount of electrolyte is provided between the patients skin and the electrode member so that electrical stability during measurement is provided.

13 Claims, 2 Drawing Sheets

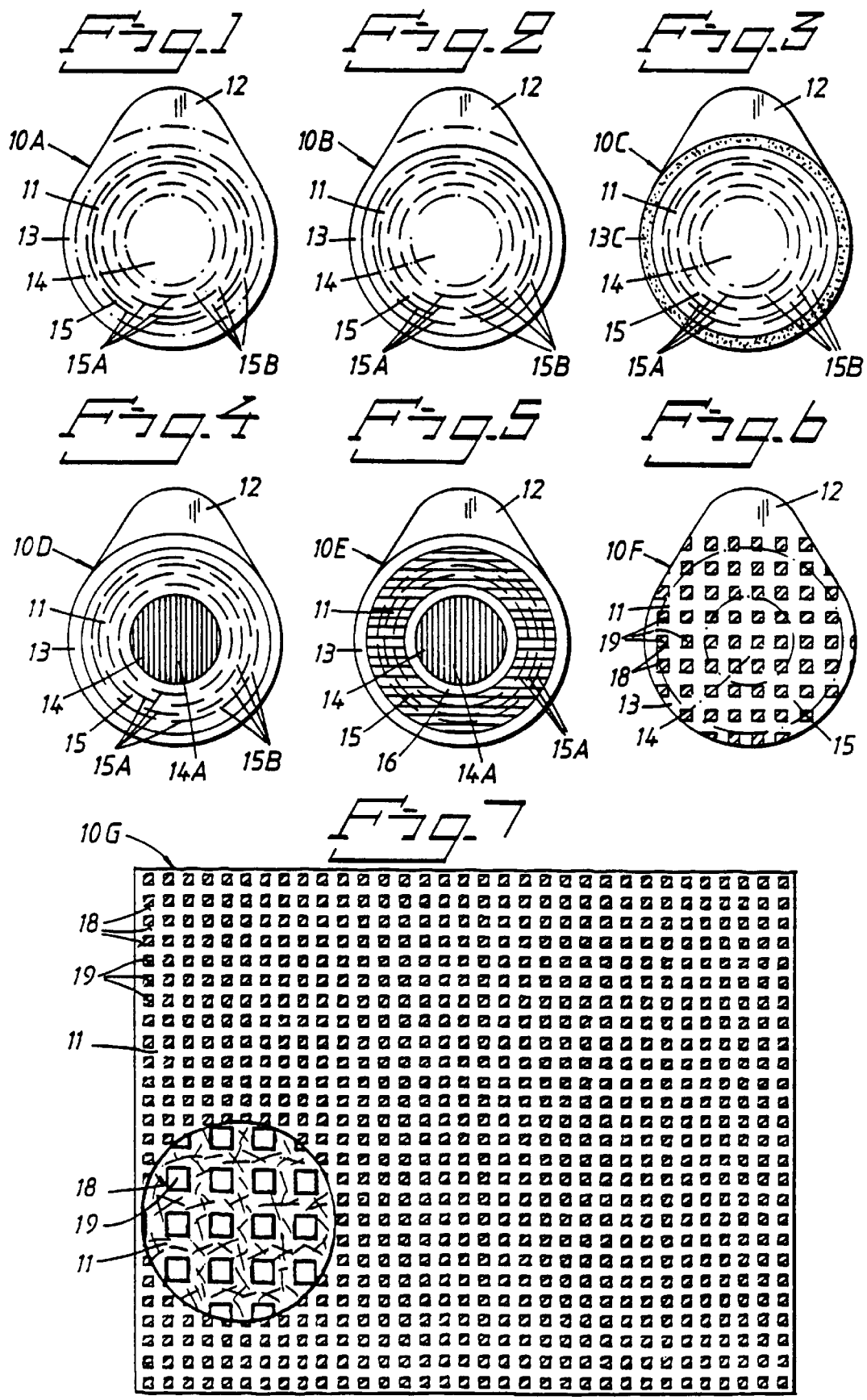

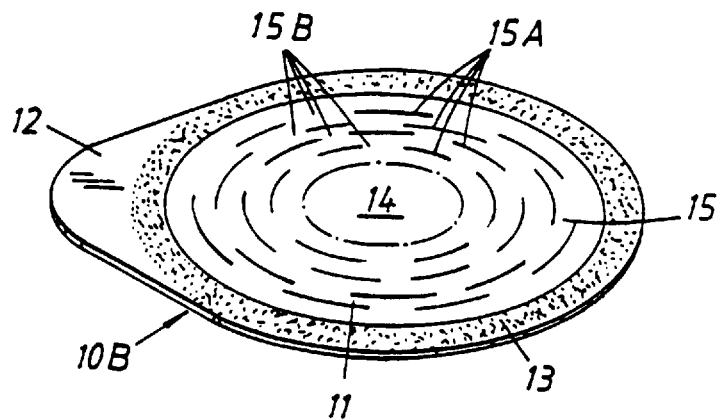
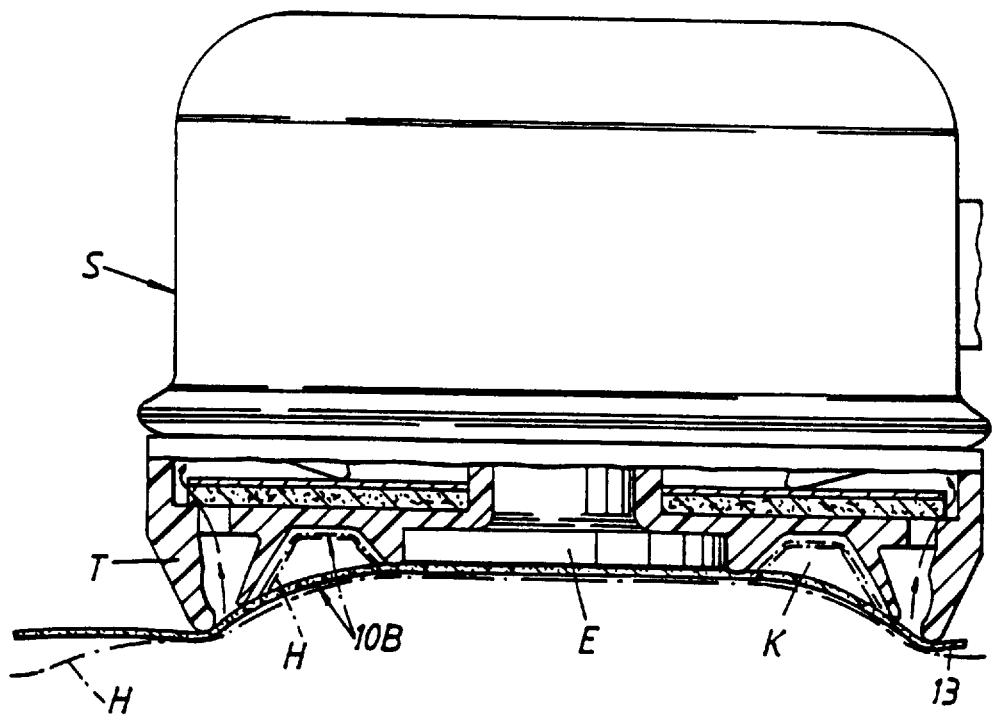

INTERFACE ELEMENT FOR A BIOMEDICAL ELECTRODE

BACKGROUND OF THE INVENTION

This invention relates to biomedical electrodes, that is, electrodes to be used for examinations or treatments in which an electrode member is electrically connected with the skin of a patient. Examples of electrodes of this kind are ECG and EEG electrodes.

The biomedical electrodes with which the invention is concerned preferably are so-called suction electrodes. Such electrodes are held to the skin by vacuum in a chamber which is delimited on the skin by a sealing device resembling a suction cup in which the electrode member is positioned. Accordingly, the invention will be described with particular reference to its use in connection with suction electrodes.

More particularly, the invention relates to a contact or interface element for use in a biomedical electrode, especially a vacuum electrode, which element is of the kind defined in the precharacterising portion of claim 1. A contact or interface element of this kind is known from GB-A-2 240 928. This known element is intended only for use with adhesive electrodes and does not lend itself to use with suction electrodes.

Moreover, the invention relates to a method for carrying out biomedical measurements using suction electrodes.

Especially when carrying out measurements using biomedical electrodes it is important have a low impedance in the electrical connection between the skin and the electrode member, but even more important is that the connection is stable throughout the measuring process in respect of the electrical properties. If variations of the electrical properties occur, they will have an adverse influence on the measuring signals.

Such variations are particularly difficult to avoid when suction electrodes are used. This is because the signals are picked up not only from the skin area engaged by the contact face of the electrode member, but also from the surrounding area, especially if sweat and electrolyte form a layer under and around the electrode member. When suction electrodes are used it is almost impossible to prevent air from leaking inwardly between the skin and the edge of the sealing device. Air that leaks in may form bubbles which migrate from the periphery of the sealing device and inwardly along the skin toward the centrally positioned electrode element and cause variations of the electrical conductivity, and possibly also dipole variations if electrostatic fields exist around the electrode member.

One proposed solution to the problem caused by the aforesaid variations involves a special design of the sealing device.

SUMMARY OF THE INVENTION

The present invention provides a different solution to the problem and involves placing between the electrode member and the skin an electrically conducting element, hereinafter termed interface element, with a high conductivity.

According to the inventive solution, the interface element is constructed such that upon application of the suction electrode the interface element is readily deformed into a domed or toroidal shape (double upward curvature) within the annular electrolyte substrate region which is situated between, on the one side, the marginal portion of the substrate (that portion of the substrate which is adapted to be placed under the annular sealing edge of the sealing device and pressed against the skin by the sealing edge) and, on the other side, the central region of the substrate (that portion of the substrate which is adapted to be positioned under the electrode member). In addition, this intermediate region is permeable to air so that it transmits the vacuum in the sealing device (the suction cup) to the underlying skin surface.

The inventive construction of the interface element ensures that the portion of the element which engages the skin between the electrode member and the sealing edge of the sealing device conforms to the domed or concave interior shape of the sealing device. Thus, the intermediate element portion can be stretched or extended or otherwise expanded or enlarged when the vacuum in the sealing device lifts the underlying skin area.

In certain embodiments, the substrate and the electrolyte are integrated in use of the interface element so as jointly to form an electrically conducting layer, the substrate material of which may be electrically conducting or nonconducting and may be in the form of a fibrous material, for example, and is thoroughly wetted or impregnated with the electrolyte such that the electrolyte wets all parts of the material and can therefore be regarded as forming a coherent layer.

In certain other embodiments, the substrate may be a "matrix", e.g. in the form of a densely perforated, conducting or nonconducting sheet material the perforations of which are filled with electrolytic material such that the electrolytic material is exposed on both sides of the substrate. The electrolytic material may be discrete bodies, but it may also be applied such that it forms a coherent layer on each side of the substrate, the two layers being interconnected by the electrolytic material in the perforations. In this case as well, the substrate and the electrolytic material may functionally be regarded as an electrically conducting layer.

In still further embodiments, the substrate may be an electrically conducting layer which is provided with a layer of electrolytic material on one or both sides. Consequently, in these embodiments the substrate and the electrolyte may functionally likewise be regarded as an electrically conducting layer or a laminate of individual layers.

Accordingly, a feature common to the three abovementioned categories of embodiments is that the substrate and the electrolyte of the ready-to-use interface element form an electrically conducting layer between the skin and the contact face of the electrode. The electrolytic material may be brought together with the substrate either during the manufacture of the interface element or immediately preceding the use thereof.

The interface element according to the invention provides a possibility of readily positioning between the patient's skin and the contact face of the electrode member an ample amount of electrolyte in a layer that remains electrically stable throughout the measuring operation and thereby promotes the stability of the signal.

In the preferred embodiment the permeability to air of the interface element substrate contributes to the electrical stability of the layer in that any air coming in beneath the interface element at the sealing device escapes directly through the interface element, instead of moving along the skin toward the contact face of the electrode member.

In one embodiment the electrolyte is not liquid, but in a solid or almost solid, suitably rubbery form and somewhat sticky or adhesive to the skin. In this embodiment the electrolyte is applied to both sides of the interface element substrate and extends through the substrate. The layer of electrolyte is thus held in a predetermined position on the interface element. In this embodiment the substrate may be made of an air-permeable absorbing material capable of absorbing sweat secreted on the skin during the measuring operation.

The interface element according to the invention also offers a hygienic advantage because no part of the suction electrode directly contacts the skin. Although the electrode member and the sealing device may become wetted by the electrolyte, they are separated from the skin and contaminants thereon.

The invention will be further illustrated by the following description of a number of different embodiments shown in the drawings.

DESCRIPTION OF THE DRAWINGS

FIG. 1–6 are diagrammatic plan views of six different embodiments of interface elements embodying the invention which are adapted for use as a disposable item;

FIG. 7 is likewise a plan view showing an interface element intended to be used for a group of electrodes positioned in a spaced-apart arrangement on one and the same patient, a portion of the interface element being drawn to a larger scale within an area surrounded by a circle;

FIG. 8 is a perspective view of the interface element of FIG. 2 as seen from the side which is adapted to engage the skin;

FIG. 9 is a cross-sectional view showing the use of the interface element of FIGS. 2 and 8 with a suction electrode.

DETAILED DESCRIPTION OF THE PREFERRED EMBODIMENT

The interface element according to the invention is lamellar, that is, the thickness of the material or material combination of which the interface element is made is a small fraction of the other dimensions (length, width, diameter) of the interface element.

FIGS. 1–6 show exemplary embodiments of interface elements all of which have a contour of the same shape, pear shape. Naturally, this shape likewise is only exemplary and many other contour shapes may be suitable. Moreover, the interface element may be preformed to have a shape different from that shown, which is initially planar. For example, it may be slightly stiffened and preformed to dome shape or some other shape exhibiting a double curvature.

In all of the embodiments shown in FIGS. 1–6 the interface element, which is designated by the numeral 10 plus a suffix letter A–F corresponding to different embodiments, can be regarded as having a circular body forming an electrolyte substrate 11 which is flexible or otherwise conformable to the skin surface, and a finger grip tab 12 which projects from and is integral with the body. In the embodiments shown in FIGS. 1, 2 and 6 there is no directly visible delimitation between the substrate 11 and the grip tab 12, but an imaginary borderline is indicated by a dash-dot line in FIGS. 1 and 2. In FIGS. 2–5 the substrate 11 has a more or less distinct circular marginal region 13 which constitutes a delimitation. In FIG. 1 the imaginary inner borderline of the marginal region 13 is represented by a dash-dot circle.

In the embodiments shown in the drawings, the interface element is intended to be applied separately to the skin, that is, before the electrode is placed over the interface element. Although the interface element is adapted to be used with a suction electrode, it is thus actually no part of the electrode. If anything, it is to be regarded as an element which is independent with regard to the suction electrode and separated therefrom until it is to be used. Preferably, the interface element is dimensioned such that the substrate 11 can accommodate within its perimeter the sealing device, or at least the electrode member, of the suction electrode.

The interface element of FIG. 1 is made from a single or multi-layered material capable of absorbing or otherwise taking up and retaining liquid, for example a fibrous material, such as tissue or other unsized paper. Materials other than cellulose fibre materials may be used, such as woven or nonwoven textile materials, and it is also possible to make the substrate 11 and the grip tab 12 from different materials and join them in a suitable manner.

In accordance with the invention, the electrolyte substrate 11 has to be able in use, that is, when it is applied to the skin, to let air pass through it. This requirement applies to the intermediate portion of the substrate located between the marginal portion of the substrate, that is, that substrate portion on which the sealing edge of the sealing device is to be placed, and the central portion of the substrate, which is the substrate portion which in use is positioned under the electrode member of the suction electrode. In the drawings, the central portion is designated by 14 (in FIGS. 1–3 and 6, in which there is no distinct physical delimitation between the central portion and the marginal portion, the central portion is indicated by a dash-dot circle), and the intermediate portion is designated by 15.

The requirement for permeability to air may be met by the material of the interface element and thus of the intermediate portion 15 of the substrate 11 being itself permeable to air.

Alternatively, or in addition to the material being inherently air-permeable, the requirement for permeability to air may be met by the intermediate portion 15 of the substrate 11 being provided with one or more slits or apertures. If such slits or apertures are provided, they should be shaped and located such that vacuum on the upper side of the substrate will be transmitted to the entire, or at least the major portion of, the skin surface under the intermediate portion 15.

In the embodiment of FIGS. 1–6, a multiplicity of arcuate slits 15A are provided in the intermediate substrate portion 15. These slits are located on a plurality of concentric circles, adjacent slits being separated by lands 15B which are narrow in relation to the length of the slits. Moreover, the slits and the lands on each circle are circumferentially offset with respect to the slits and lands of adjacent circles.

The illustrated pattern of arcuate slits not only ensures good permeability to air throughout the surface of the intermediate portion 15, but also ensures that the intermediate portion, without becoming torn apart or subjecting the marginal portion 13 or the central portion 14 to excessive forces, can adapt to the shape which the underlying skin adopts under the action of the vacuum in the sealing device. This shape may vary depending on the shape of the sealing device but may be generally designated as dome or toroidal shape. When vacuum is applied to the sealing device, that the portion of the skin which is subjected to the vacuum will be drawn upwardly with respect to the skin portion which is beneath the sealing edge of the sealing device. This upward drawing of the skin may be opposed or limited by the electrode member.

The illustrated pattern of arcuate slits is only an example; other slit patterns, such as zig-zag or herringbone patterns may also be used.

In use, when the interface element is applied to the skin, the substrate 11 shall incorporate or support a layer of electrolyte. In some embodiments the electrolyte is liquid while in other embodiments it is viscous or gel-like and in still further embodiments it is solid or almost solid and slightly adhesive to the skin.

In the embodiment of FIG. 1 and some of the other illustrated embodiments, a layer of liquid electrolyte may be provided by impregnating the interface element material with a suitable water-soluble electrolytic material during the manufacture of the interface element. Immediately before the interface element is placed on the skin, the interface element is dipped in water so that the substrate will contain an aqueous solution of the electrolytic material.

It is also conceivable and feasible instead to dip the interface element in a ready-made electrolytic solution immediately before the interface element is used.

In use of the interface element, following the dipping, the interface element is placed on the area of the patient's skin where an electrode is to be applied, whereupon the electrode is placed over the interface element such that the sealing device will be located inside the perimeter, on the marginal portion 13, of the interface element. This in shown in FIG. 9 in respect of the interface element 10B, which may be regarded as representative of the basic mode of function, the suction electrode being generally designated by S (it may be of the type disclosed in WO93/16633). The electrode member of the suction electrode is designated by E and the sealing device thereof is designated by T. The vacuum chamber defined by the sealing device T is designated by K. The illustrated suction electrode S is only one example of an embodiment of a suction electrode which may be used with the interface element according to the invention.

Because of the air-permeability of the interface element 10B, the vacuum in the vacuum chamber K of the suction electrode will be transmitted to the skin over the entire or almost entire skin surface, and the skin inside the sealing device T, and thereby also the interface element, will be lifted as shown in FIG. 9 so that the electrode member E will be pressed against the upper side of the interface element. If the vacuum remains applied for a sufficient time, the skin, and thus the intermediate portion 15 of the interface element will be lifted such that the skin will press the entire intermediate portion of the interface element against the inside of the sealing device as is indicated by a dash-dot line in FIG. 9.

After the measurement, the suction electrode is removed and the interface element is taken away and discarded.

The interface element in FIG. 2 differs from the interface element 10A only in that it is stiffened over the marginal portion 13 of the substrate 11 and the fingergrip tab 12. This stiffening primarily serves to making the interface element easier to handle and to reduce the risk of tearing it. However, a suitable degree of stiffening and/or preparation may also contribute to reducing the risk of inward air leakage at the sealing member of the suction electrode. The stiffening may be brought about in any suitable manner, such as by compressing the material.

The interface element 10C of FIG. 3 is stiffened like the interface element 10B and additionally treated such that is has a certain, relatively weak tackiness or other kind of adhesivity to the skin over the circular marginal portion 13C on at least one side. This adhesivity, which is indicated by dotting of the marginal portion 13C, should preferably not be stronger than is required to keep the interface element in position on the skin when the suction electrode is being applied to it. If the interface element is held too firmly to the skin, its removal may be unnecessarily painful or uncomfortable to the patient.

In the interface element 10D of FIG. 4, the central portion of the substrate 11 is provided with a circular pad 14A (marked by vertical hatching of the central portion 14) of a relatively firm but yet slightly mouldable electrolyte which exhibits a certain tackiness or adhesivity to the skin. This pad may advantageously be applied in such manner during the manufacture of the interface element that it is exposed on both sides of, and extends through, the substrate. Otherwise, the interface element 10D is similar to the interface element 10A, 10B or 10C.

The interface element 10E of FIG. 5 differs from the interface element of FIG. 4 in that the electrolyte pad 14A is surrounded by an electrically insulating zone 16 and in that the intermediate portion 15 of the substrate forms a zone having an enhanced absorptivity. This zone is marked by horizontal hatching of the intermediate portion and serves to take up sweat coming out of the skin during the measurement.

FIG. 6 shows an interface element 10F the substrate 11 of which is made of a fibrous material and has openings 18 accommodating throughgoing "islands" 19 of electrolytic material of the same kind as that in FIGS. 4 and 5. The islands 19 are exposed on both sides of the substrate 11 and interconnect the skin and the contact face of the electrode member. The substrate zones separating the openings 18 and the islands 19 accommodated therein function as both air-permeable and electrically insulating zones. By their tackiness or adhesivity to the skin, the small electrolyte islands 19 contribute to keeping the interface element 10F in position on the skin without at the same time causing the removal of the interface element upon completion of the measurement to be uncomfortable.

FIG. 7 shows an interface element 10G according to the invention which is suitable for use when a plurality of closely spaced electrodes are to be applied to the skin. The substrate 11 is in the form of a sheet or strip which is provided with a large number of openings 18 and electrolyte islands 19 accommodated therein as in the substrate 11 of FIG. 6. In this case it of course is important that the substrate 11 is constructed such that the electrolyte islands 19 are well insulated from one another and that short-circuiting between the electrodes during the measurement is avoided. It may therefore be advantageous to have the electrolyte islands arranged in groups which are spaced apart, for example in accordance with the pattern in which the electrodes are to be placed on the body.

In the embodiments of FIGS. 6 and 7, the substrate is made of a nonwoven type of material in which the fibres are so loosely bonded that the substrate can readily be stretched or expanded sufficiently for the intermediate portion of the interface element to conform to the shape which the underlying skin portion adopts under the influence of the vacuum, without adversely influencing the surrounding marginal portion or the central portion.

Suitably, the interface elements 10D, 10E, 10F and 10G are provided with a removable protective layer (not shown) on both sides so that drying up of the electrolyte gel is prevented.

Within the scope of the invention, that side of the substrate which faces away from the skin during the measurement may be provided with a metal coating over the area which is to be engaged by the electrode member E. Instead of the illustrated full electrode member, the suction electrode may then have a contact element which is engaged with the metal coating when the suction electrode is placed on the interface element. In such a case it may be sufficient for the interface element to cover an area of the skin which is smaller than the skin area which is delimited by the sealing device of the suction electrode.

Within the scope of the invention is also an embodiment of the method and the interface element according to the invention in which a plurality of preferably discoid electrolyte bodies, one for each electrode, are attached to a sheet or strip substrate such that they are readily releasable therefrom, these bodies preferably being covered on their side facing away from the substrate by a removable protective sheet. The pattern is adapted to the pattern according to which electrodes are to be applied.

In this case the electrolyte bodies are of the relatively firm, tacky or adhesive type mentioned above, and they may advantageously be provided with a metal coating on the side facing the substrate.

When a measurement is to be carried out, the protective sheet, if present, is removed, whereupon the substrate is placed on the skin of the patient with the exposed side of the electrolyte bodies facing away from the substrate engaging the skin. The electrolyte bodies are pressed onto the skin by a light finger pressure on the substrate. The substrate is then lifted away, the electrolyte bodies remaining on the skin. The electrodes may then be applied in the desired predetermined pattern by placing them over respective ones of the electrolyte bodies and attaching them by vacuum.

After the measurement has been completed and the suction electrodes have been taken away, the electrolyte bodies can readily be removed from the skin. The removal can be facilitated if the electrolyte bodies are provided with a fingergrip tab, such as one formed by a lobe of the metal layer where such a layer is provided.

What is claimed is:

1. An interface element for use with a biomedical electrode comprising:
    a lamellar substrate for an electrolyte including a skin contact surface and an opposed electrode contact surface, said substrate further including a central portion, a peripheral margin portion and an intermediate portion disposed between the central portion and the peripheral margin portion, the peripheral margin portion being adapted to form a vacuum seal against skin of a patient with a seal portion of an applied biomedical suction electrode, and the intermediate portion being permeable to air and expandable to a domed shape such that upon forming a seal with a biomedical suction electrode, any air disposed between a patient's skin and the skin contact surface may be evacuated.

2. An interface element as defined in claim 1, wherein the intermediate portion comprises a plurality of slits.

3. An interface element as defined in claim 1, wherein the intermediate portion comprises a woven or non-woven fibrous material.

4. An interface element as defined in claim 1, wherein the substrate is impregnated with a water soluble, solid electrolyte.

5. An interface element as defined in claim 1, wherein the substrate comprises a liquid absorbing material.

6. An interface element as defined in claim 1, wherein the peripheral margin portion is stiffened.

7. An interface element as defined in claim 1, wherein the substrate further comprises an annular adhesive zone on the skin contact surface in the peripheral margin portion.

8. An interface element as defined in claim 1, wherein the central portion comprises a pad of electrolytic gel.

9. An interface element as defined in claim 8, wherein the pad of electrolytic gel is circumscribed by an electrically insulating substrate zone.

10. An interface element as defined in claim 1, wherein the substrate comprises a multiplicity of through openings which are filled with an electrolytic gel.

11. An interface element as defined in claim 10, wherein the substrate is dimensioned to accommodate a plurality of biomedical suction electrodes placed side by side thereon.

12. An interface element as defined in claim 1, wherein the substrate has a generally circular configuration and further comprises a projecting finger grip portion projecting therefrom.

13. A method for making biomedical measurements, comprising the steps of:
    providing a suction electrode including a vacuum chamber with an edge seal portion and a central recessed electrode portion;
    providing an interface element comprising a lamellar substrate for an electrolyte including a skin contact surface and an opposed electrode contact surface, said substrate further comprising a central portion, a peripheral margin portion and an air permeable intermediate portion disposed between the central portion and the peripheral margin portion;
    applying the lamellar substrate to a patient with the skin contact surface against the patient's;
    applying the suction electrode on the lamellar substrate so that the edge seal portion engages the peripheral margin portion;
    evacuating the vacuum chamber to remove any air disposed between the patient's skin and the skin contact surface through the intermediate portion and to draw the skin and intermediate portion inwardly into the vacuum chamber so that the central portion of the electrode contact surface contacts the central recessed electrode portion, thereby securing the suction electrode to the skin of the patient for biomedical measurement.

* * * * *